United States Patent
Bosma et al.

[11] Patent Number: 6,099,549
[45] Date of Patent: Aug. 8, 2000

[54] VASCULAR FILTER FOR CONTROLLED RELEASE

[75] Inventors: Gjalt Bosma, Opeinde; Hendrik G. Breedveld, Groningen, both of Netherlands

[73] Assignee: Cordis Corporation, Miami, Fla.

[21] Appl. No.: 09/330,488

[22] Filed: Jun. 11, 1999

[30] Foreign Application Priority Data

Jul. 3, 1998 [NL] Netherlands .......................... 1009551

[51] Int. Cl.[7] ................................................ A61M 29/00
[52] U.S. Cl. .................................... 606/200; 606/191
[58] Field of Search ................................ 606/191, 198, 606/194, 199, 200; 604/104; 623/1, 11, 4, 12

[56] References Cited

U.S. PATENT DOCUMENTS

| | | | |
|---|---|---|---|
| 4,957,501 | 9/1990 | Lahille et al. | 606/200 |
| 5,234,458 | 8/1993 | Metais | 606/200 |
| 5,350,398 | 9/1994 | Pavcnik et al. | 606/200 |
| 5,413,586 | 5/1995 | Dibie et al. | 606/200 |
| 5,531,788 | 7/1996 | Dibie et al. | 606/200 |
| 5,709,704 | 1/1998 | Nott et al. | 606/200 |

FOREIGN PATENT DOCUMENTS

| | | |
|---|---|---|
| 0 165 713 | 12/1985 | European Pat. Off. . |
| 0 348 295 | 12/1989 | European Pat. Off. . |
| 0 350 043 A1 | 1/1990 | European Pat. Off. . |
| 0 815 803 A1 | 1/1998 | European Pat. Off. . |
| 40 30 998 A1 | 4/1991 | Germany . |
| 195 09 464 C1 | 6/1996 | Germany . |
| 92/14408 | 9/1992 | WIPO . |
| 94/06502 | 3/1994 | WIPO . |
| 98/02112 | 1/1998 | WIPO . |

*Primary Examiner*—Gary Jackson
*Attorney, Agent, or Firm*—Michael W. Montgomery

[57] ABSTRACT

The present invention relates to a vascular filter which can be placed inside a body cavity, such as a blood vessel. A catheter may be used to deliver the filter, and consists of a tubular basic body with a distal end, a proximal end and a lumen extending between the ends. The vascular filter may be received in a compressed state inside the catheter lumen. The catheter may include an ejection device, which can be used to eject the vascular filter from the distal end of the catheter. Some portion of the vascular filter may tend to push off in a resilient manner against the distal end of the catheter, and the filter preferably includes a brake for acting on the catheter lumen, which tends to slow and control ejection from the catheter.

9 Claims, 4 Drawing Sheets

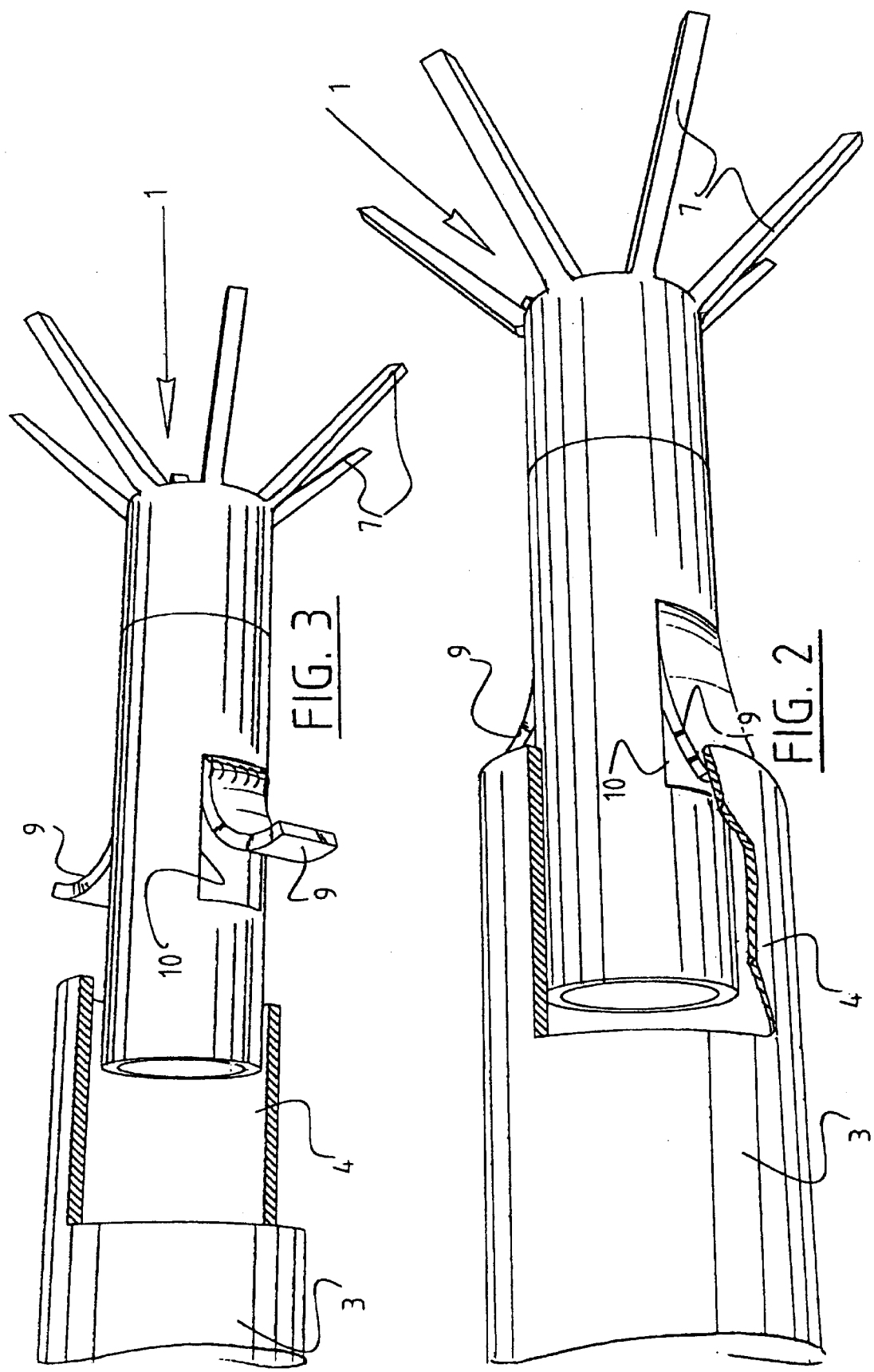

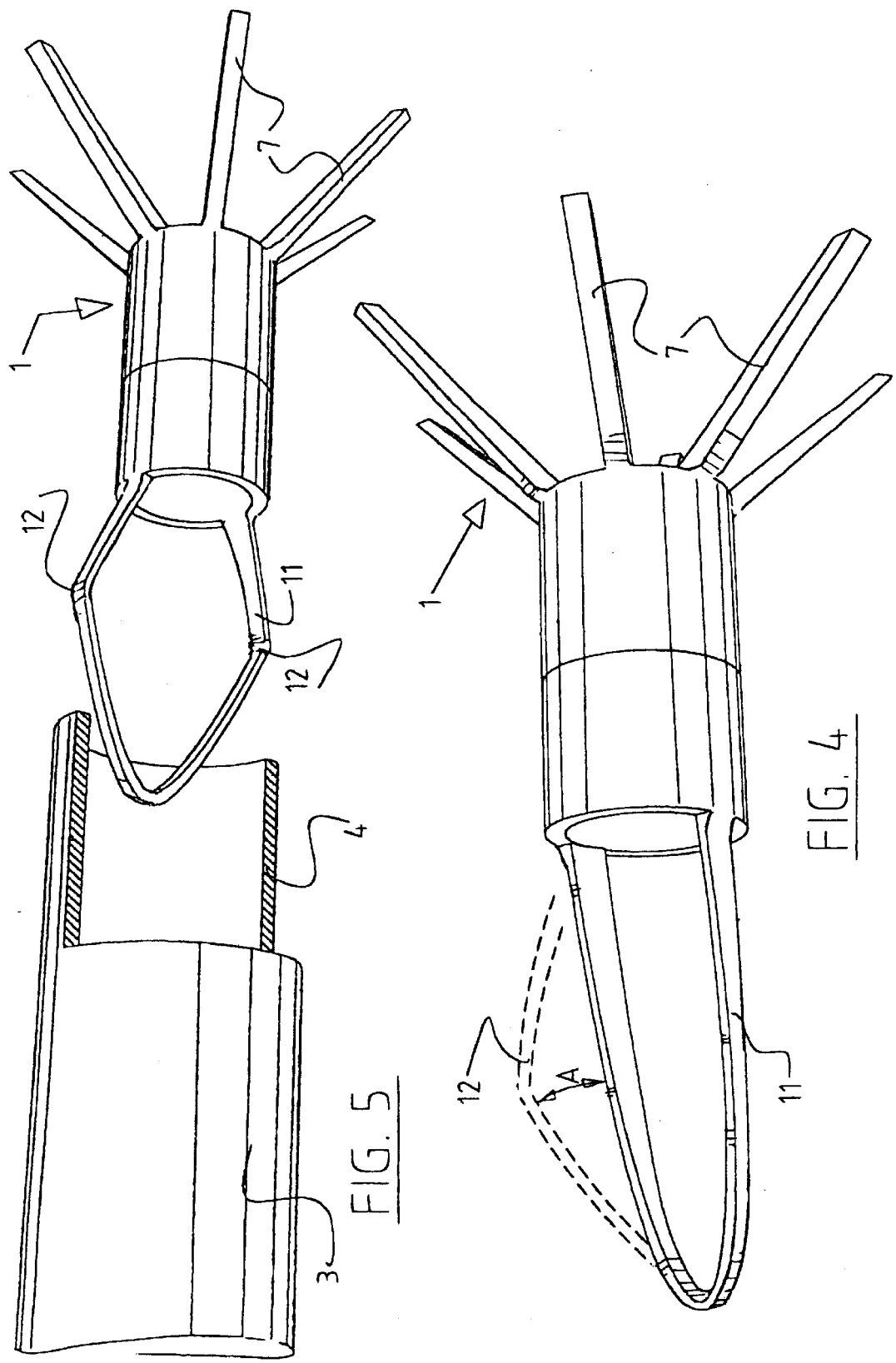

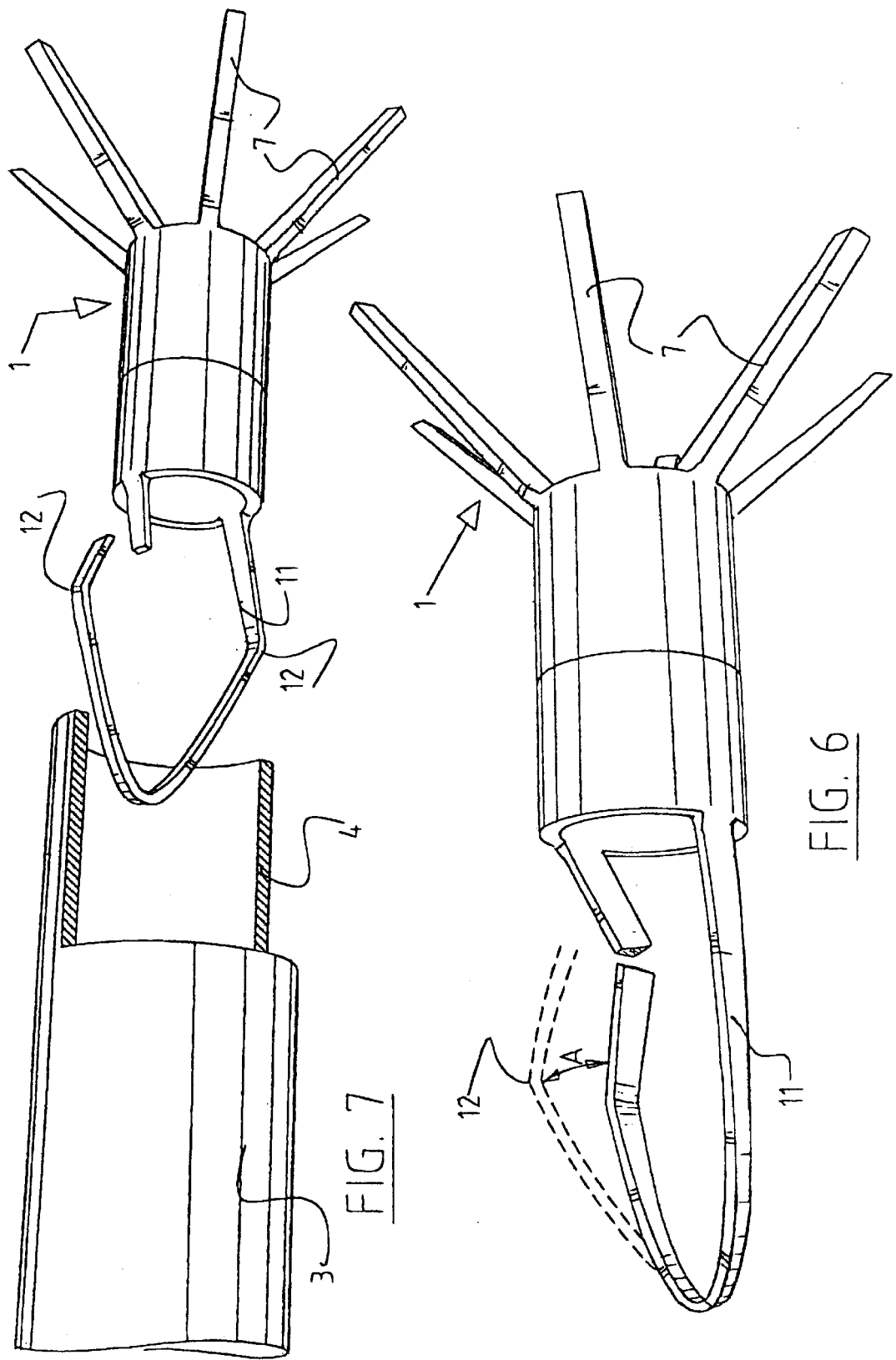

VASCULAR FILTER FOR CONTROLLED RELEASE

BACKGROUND AND SUMMARY OF THE INVENTION

1. Technical Background

The present invention relates generally to medical devices, and more particularly to a vascular filter and delivery system.

2. Discussion

Vascular filters may be used for a variety of therapeutic applications, including implantable vena cava filters for capturing thrombus, or for distal protection during a vascular procedure.

The present invention relates to a filter system including a vascular filter that can be placed inside a body passage or cavity, such as a blood vessel, through a catheter consisting of a tubular basic body with a distal end, a proximal end and a lumen extending in between the ends. The vascular filter can be received in a compressed state inside the lumen, and the catheter is provided with an ejection device which can be used to eject the vascular filter from the distal end of the catheter. The filter may be implanted either permanently or temporarily.

Vascular filters are often made of an elastic or so-called "memory" material. Prior to actually positioning the vascular filter according to the known technique inside the blood vessel, the filter is arranged in a compressed state in the catheter. By means of an ejection member, the filter may be pushed from the open distal tip of the catheter into the blood vessel.

Many prior vascular filters expand from the compressed state inside the catheter lumen to an enlarged or deployed state, when released or deployed at the desired site for treatment. Some vascular filters tend to resiliently expand to that deployed state, which facilitates ejection from the catheter. Also, this resilient outward pressing may resist longitudinal movement from the desired site or compressive external forces.

It is also possible, however, that the resilient expansion by a filter may cause it to push off in a resilient manner against the distal end of the catheter. This possible longitudinal pushing or jumping tendency may cause a vascular filter to rest in some location other than the desired site. Consequently, accurate positioning of the filter inside the blood vessel may require some measure of skill.

Accordingly, it is desirable to provide a vascular filter capable of being more easily positioned accurately, and which tends to proceed smoothly and predictably during deployment.

One embodiment of the present invention is therefore to provide a vascular filter for use with a catheter to introduce the filter, wherein a brake is provided. The brake acts between the filter and catheter which may tend to control ejection by means of engaging the lumen. This engagement may of course be frictional, and the brake may be provided on the filter or the catheter, or may consist of cooperating components on both filter and catheter.

With a vascular filter and catheter system according to the present invention, an accelerating force exerted by the vascular filter on the distal tip of the catheter can be resisted or even negated by the brake. The brake preferably frictionally opposes the movement of the filter out of the catheter. Consequently any expansive accelerating force exerted during ejection of the filter is controlled, at least any particular expansive force which may cause an unexpected longitudinal advance in relation to the distal tip of the catheter.

The brake may have any of a number of embodiments, as will be discussed in the detailed explanation below which are given by way of example. For example, the brake may have been biased, or the brakes may form a unit with the filter, or may act in unison with additional brakes.

These and various other objects, advantages and features of the invention will become apparent from the following description and claims, when considered in conjunction with the appended drawings.

BRIEF DESCRIPTION OF THE DRAWINGS

FIGS. 2 and 3 are partial perspective views of a vascular filter and catheter system according to one embodiment of the present invention, showing operation of a braking system;

FIG. 4 is a perspective view of a vascular filter, showing another embodiment of the present invention;

FIG. 5 is a partial perspective view of a vascular filter and catheter system arranged according to the principles of the present invention, after the filter has been ejected from the catheter;

FIG. 6 is a perspective view of a vascular filter, according to another embodiment of the present invention; and FIG. 7 is a partial perspective view of the vascular filter and catheter system of FIG. 6, after the filter has been ejected from the catheter.

DETAILED DESCRIPTION OF THE PREFERRED EMBODIMENT

Figure 1:
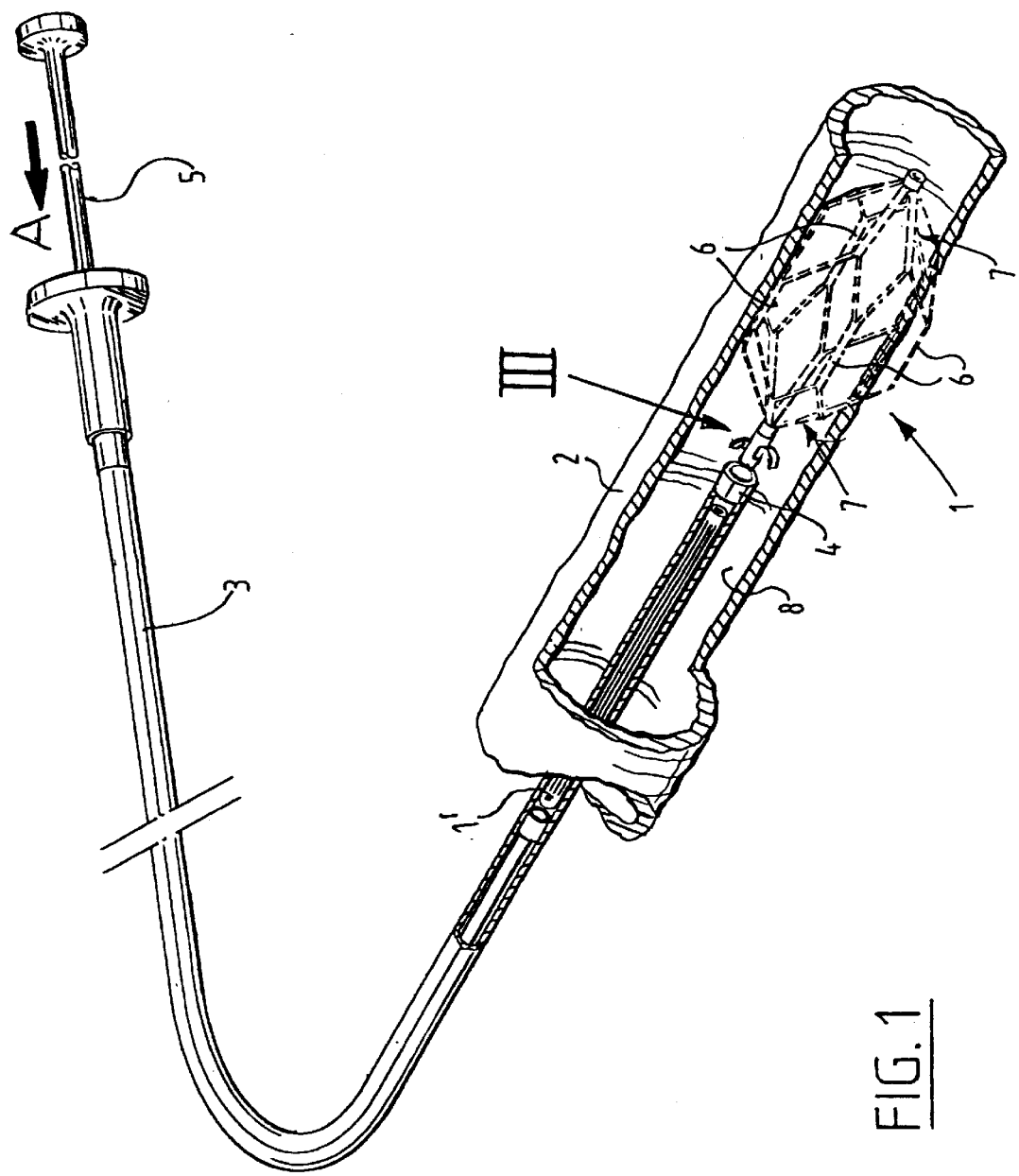
FIG. 1 is an external perspective view of a vascular filter and catheter system, arranged according to the principles of the present invention and in a position of use.

The following description of the preferred embodiments of the present invention is merely illustrative in nature, and as such does not limit in any way the present invention, its application, or uses. Numerous modifications may be made by those skilled in the art without departing from the true spirit and scope of the invention.

Referring to the drawings, in FIG. 1 a vascular filter 1 according to the present invention has been illustrated. In the situation illustrated, the vascular filter 1 has just been introduced into a blood vessel 2 by means of a catheter 3, which is substantially hollow. In the distal tip 4 of the catheter 3, at least one vascular filter was initially arranged in a compressed state. As an alternative (not illustrated), it is also possible that the filter is pushed along the entire length of the catheter from its proximal end to its distal end, after the catheter distal end has been advanced to the desired position. Preferably the filter is packed, in a compressed state, in transport packaging forming a covering. The vascular filter may be ejected from the distal tip 4 of the catheter 3 by means of a pushing wire 5 and introduced into the blood vessel. Due to release from the radially compressive force imposed by the lumen at the distal tip 4 of the catheter 3, the vascular filter 1 will tend to expand resiliently to obtain an expanded shape.

The vascular filter illustrated here comprises a number of ribs 6 extending in an axial direction in relation to the blood vessel 2 and along the internal wall hereof. These ribs 6 form an elongated body member. On either side of the ribs 6, filters 7 have been arranged each forming a grid shape. Liquid inside the blood vessel can pass through in an unimpeded fashion, but thrombus will tend to be intercepted by one of the two filters 7.

An advantage of this configuration is that it provides two chances at intercepting thrombus moving inside the blood vessel. In addition, due to the configuration of the ribs 6 which extend along the internal wall of the blood vessel 2, there should be no free ends of ribs which might stick into the internal wall of the blood vessel 2. The configuration of the vena cava filter according to the present invention illustrated is consequently designed so as to minimize any distress or damage to the blood vessel inside of which it has been arranged. As filters 7 have been arranged on either side of the ribs 6, and consequently a symmetrical shape has been obtained, there is no difference in the performance of the filter regarding the direction from which this vascular filter 1 has been placed inside the blood vessel 2.

As has been illustrated here clearly, the grid shape of each of the filters 7 is such that each of the ribs 6 is connected with a number of the components of these filters. Furthermore, each of the ribs 6 is connected with both filters 7 on either side. Due to this configuration, an added safety feature is that one of the ribs 6 or a component of one of the filters 7 may even break without a part of the filter 1 separating as a consequence.

In addition, tipping over or misalignment of either filter is less likely due to the more or less tubular shape into which the ribs 6 have been arranged, so that positioning of the vascular filter 1 inside the blood vessel 2 can take place with unprecedented stability and reliability.

The vascular filter 1 is preferably made of a very resilient material, like nitinol. Following ejection from the distal tip 4 of the catheter 3, filter 1 can expand and will be wedged against the internal wall 8 of the blood vessel 2.

In accordance with embodiment of the present invention shown in FIG. 1, two projections 9 form a resilient brake, arranged close to the proximal end of the vascular filter 1. These resilient projections 9 serve in particular to control ejection of the proximal section of the filter 1.

The projections 9 push against the inside of the catheter lumen close to the distal end of the catheter 3. The proximal filter 7 may tend to exert a force on the distal edge of the catheter 3 during ejection of the filter 1. In this way the projections 9 slow down the rate of expansion, and thus control the expansive force of the filter 7. Thus, accuracy when positioning a vascular filter according to the present invention may be improved.

In the embodiment shown in FIGS. 2 and 3, the projections 9 have been biased and extend in an outward radial direction in relation to the proximal end section of the filter 1, so that they push against the internal wall of the catheter 3, before escaping from the catheter themselves. These outwardly directed projections 9 consequently cause a braking force on the internal wall of the catheter 3, which is also directed outwards, so that control of the ejection of the filter 1 is effected.

The projections 9 form a unit with the filter 1, in the sense that each of the projections 9 has been made of material from the filter 1 located in between closely arranged cuts 10. The strips of material from the cuts 10 have subsequently been biased.

The filter 1 shown in the Figures has been made of a cylindrical unit. As an alternative, the filter may have been made from a plate-like unit or from an assembly of rib-like elements. Other options are possible as well. The filter may have been made of a resilient material, such as nitinol, which expands into the filter 1 with the shape illustrated here, following ejection of the cylindrical body 1'. As an alternative or as an addition, different types of memory materials, or other shape-memory metals, may be used.

The projections 9 are positioned radially opposite each other near to the proximal end of the filter 1, so that as a consequence a more uniformly distributed force is exerted on the internal wall of the catheter 3. To this end also, more than two projections 9 may be employed. In FIG. 2, the action of the projections 9, which push from the proximal end of the filter 1 against the internal wall of the distal end 4 of the catheter 3, has been illustrated schematically. As has already been mentioned before, this braking effect is preferably present especially during the release and expansion of the proximal filter 7 of the vena cava filter 1 according to the present invention. The projections 9 tend to slow down the ejection speed of the vascular filter 1, which is caused by elements of the proximal filter 7 pushing off against the extreme edge of the catheter 3 at the distal end hereof.

FIG. 3 shows the situation illustrated in FIG. 2 during a slightly later stage, and it is clear that the projections 9 pushed against the internal wall of the catheter 3 with a certain force. This situation is evidenced by confirming that the projections 9 protrude more than the internal dimensions of the catheter 3, in the state illustrated in FIG. 3. The compression of the projections 9 illustrated in 2 consequently ensures that a braking force is exerted on the internal wall of the catheter 3, which tends to control expansion of the proximal filter 7.

In the embodiment of the vascular filter 1 according to the present invention illustrated in FIG. 4, the brake is formed as a single loop 11. The loop 11 is resilient in the sense that it has a tendency to expand from the state drawn with continuous lines, in the direction indicated by arrow A, into the state drawn with dotted lines. In FIG. 4, the loop 11 has been illustrated in a state which corresponds to transportation inside the catheter 3 to the desired position. In contrast, the state of the loop 11 indicated with dotted lines corresponds to the relaxed situation, in which the vascular filter 1 has been ejected into the blood vessel. This last situation has been illustrated in greater detail in FIG. 5, in which the vascular filter 1 and the proximal filter 7 with its loop 11 have expanded in a controlled manner.

It should be noted that by the time that the bending points 12 of the loop 11 pass the extreme distal edge of the catheter 3, the majority of the vascular filter, and in particular proximal filter 7, will have already secured itself against the wall of the blood vessel. Any longitudinal force due to expansion of the loop 11, after the bending points 12 have been ejected beyond the distal tip of the catheter 3, is consequently cushioned by the proximal filter 7 being stabilized inside the blood vessel 2.

One advantage of the embodiment of a vascular filter according to the present invention illustrated in the FIGS. 4 and 5 is that the loop 11 may be used to later remove the vascular filter 1. Loop 11 can thus serve as a target for a hook-shaped extraction element, in order to remove the vascular filter 1. The hook-shaped extraction body (not shown) may engage the loop 11, and pull the entire vascular filter 1 back into a catheter enveloping the extraction element.

After reading the above, many possible embodiments which may be used to control the ejection speed during expansion of certain components, other embodiments and features will occur to one of ordinary skill in the field. All of these are to be considered as falling within the scope of the attached claims. It is for instance possible to use a vascular filter which has a different shape than the one described above. It is also possible to use a more conventional vascular filter without the double filter-function. The vascular filter also does not need to comprise ribs extending in an axial direction in relation to the blood vessel.

Also, one or more removal members may be added at the distal end of the vascular filter, which may have been embodied in the shape of a hook or a loop. Such a removal member can be gabbed from the other side or the distal side such that removal of the filter is possible.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A vascular filter for delivery through a catheter to a desired site in a body vessel for therapeutic treatment of a patient, comprising:

a base member;

at least one filter element coupled to the base member, the filter element having a compressed shape and an expanded shape, and the filter element tending to resiliently expand from the compressed shape to the expanded shape, such that when the filter element is positioned at the desired site and immersed in a body fluid flowing past the desired site, the filter element is adapted to filter the body fluid; and at least one brake coupled to the base member, wherein the brake extends radially outward in a relaxed configuration, and tends to resiliently press radially outward when in a compressed configuration.

2. The vascular filter as set forth in claim 1, wherein the filter is integral and unitary.

3. The vascular filter as set forth in claim 1, wherein at least a portion of the filter has been made of nitinol.

4. The vascular filter as set forth in claim 1, wherein said brake is formed as a resilient loop.

5. A filter delivery system for delivery and deployment of a vascular filter through a catheter to a desired site in a body vessel for therapeutic treatment of a patient, comprising:

a catheter having proximal and distal ends, the catheter defining a lumen extending between the catheter proximal and distal ends;

a filter disposed within the catheter lumen in a compressed shape; and an ejection member slidably received within the catheter lumen, the ejection member being selectively actuable to push the filter out the catheter distal end into the body vessel in the region of the desired site;

wherein the filter has a filter element tending to resist movement of the filter form the catheter; in a body fluid flowing past the desired site, the filter element is adapted to filter the body fluid;

and wherein the filter has at least one brake tending to resist movement of the filter from the catheter; thereby controlling the motion of the filter during delivery to the desired site.

6. The filter delivery system as set forth in claim 5, wherein the brake tends to resiliently press radially outward against an inner wall of the catheter lumen and includes at least one projection close to the proximal end of the filter.

7. The filter delivery system as set forth in claim 6, wherein the projection has been biased in an outward direction in relation to the filter in the compressed state.

8. The filter delivery system as set forth in claim 5, wherein at least one additional projection has been arranged close to the proximal end.

9. The filter delivery system as set forth in claim 8, wherein the projection and the additional projection have been arranged on the filter at radially opposite sides.

* * * * *

UNITED STATES PATENT AND TRADEMARK OFFICE
CERTIFICATE OF CORRECTION

PATENT NO. : 6,099,549
DATED : August 8, 2000
INVENTOR(S) : Bosma, et al.

It is certified that error appears in the above-identified patent and that said Letters Patent is hereby corrected as shown below:

```
Column 6, line 16
     movement of the filter form

Should read:
     movement of the filter from
```

Signed and Sealed this

Ninth Day of January, 2001

*Attest:*

Q. TODD DICKINSON

*Attesting Officer*   *Commissioner of Patents and Trademarks*